(12) United States Patent
Haslam et al.

(10) Patent No.: US 7,465,465 B2
(45) Date of Patent: Dec. 16, 2008

(54) PHARMACEUTICAL FORMULATION COMPRISING LANTHANUM COMPOUNDS

(75) Inventors: Robert Paul Haslam, Pewsey (GB); Laura Anna Trespidi, Pizzighettone (IT); Josephine Christine Ferdinando, Tadley (GB)

(73) Assignee: Shire Biochem Inc., Laval, Quebec (CA)

( * ) Notice: Subject to any disclaimer, the term of this patent is extended or adjusted under 35 U.S.C. 154(b) by 0 days.

(21) Appl. No.: 10/926,330

(22) Filed: Aug. 26, 2004

(65) Prior Publication Data

US 2005/0079135 A1 Apr. 14, 2005

Related U.S. Application Data

(60) Provisional application No. 60/497,560, filed on Aug. 26, 2003, provisional application No. 60/517,078, filed on Nov. 5, 2003.

(51) Int. Cl.
*A61K 31/26* (2006.01)
*A61K 9/20* (2006.01)
*A61K 33/00* (2006.01)
*A01N 55/02* (2006.01)
*A01N 59/00* (2006.01)

(52) U.S. Cl. ............... 424/600; 424/464; 424/715; 514/492

(58) Field of Classification Search ........ 424/464, 424/715; 514/960, 492
See application file for complete search history.

(56) References Cited

U.S. PATENT DOCUMENTS

| | | | |
|---|---|---|---|
| 4,822,594 A | 4/1989 | Gibby | |
| 4,877,735 A | 10/1989 | Nogami et al. | |
| 5,853,758 A * | 12/1998 | Lo | 424/464 |
| 5,968,976 A | 10/1999 | Murrer et al. | |
| 6,703,005 B2 | 3/2004 | Allan et al. | |
| 2001/0014352 A1 | 8/2001 | Batra et al. | |
| 2002/0051822 A1* | 5/2002 | Atherton et al. | 424/600 |
| 2002/0122823 A1 | 9/2002 | Bunick et al. | |
| 2002/0155168 A1* | 10/2002 | Abrams et al. | 424/617 |
| 2003/0186845 A1 | 10/2003 | Yoshida | |
| 2004/0029829 A1 | 2/2004 | Miyazaki et al. | |
| 2004/0043971 A1 | 3/2004 | Mazess et al. | |
| 2004/0120922 A1 | 6/2004 | Burke | |
| 2004/0161474 A1 | 8/2004 | Moerck et al. | |
| 2005/0096438 A1 | 5/2005 | Chang et al. | |
| 2005/0131138 A1 | 6/2005 | Connor et al. | |
| 2005/0147580 A1 | 7/2005 | Connor et al. | |
| 2005/0208080 A1 | 9/2005 | Heightman et al. | |
| 2005/0209423 A1 | 9/2005 | Chang et al. | |
| 2005/0220750 A1 | 10/2005 | Robert et al. | |
| 2005/0220751 A1 | 10/2005 | Charmot et al. | |
| 2005/0220889 A1 | 10/2005 | Charmot et al. | |
| 2005/0220890 A1 | 10/2005 | Charmot et al. | |

| | | |
|---|---|---|
| 2005/0239901 A1 | 10/2005 | Chang et al. |
| 2006/0121127 A1 | 6/2006 | Ferdinando et al. |

FOREIGN PATENT DOCUMENTS

| | | | |
|---|---|---|---|
| CA | 2 216 437 C | | 10/1996 |
| EP | 295861 | | 12/1988 |
| EP | 299910 | | 1/1989 |
| EP | 1 267 662 A | | 10/2001 |
| EP | 1 344 528 | | 9/2003 |
| GB | 0015745 | | 8/2000 |
| JP | 62-145024 | * | 6/1987 |
| JP | 62145024 | | 6/1987 |
| JP | 1085088 A | | 3/1989 |
| JP | 8070851 | | 3/1996 |
| JP | 200247210 | | 2/2002 |
| JP | 2002-187838 A | | 7/2002 |
| JP | 2002-193735 A | | 7/2002 |
| KR | 10-1997-0706684 | | 6/2002 |
| WO | WO 96/30029 | * | 10/1996 |
| WO | WO-98/00104 A | | 1/1998 |
| WO | WO 99/15189 | * | 4/1999 |
| WO | WO-01/76409 A1 | | 10/2001 |
| WO | WO-02/00227 | | 1/2002 |
| WO | WO-02/49656 | | 6/2002 |
| WO | WO-02/085348 A1 | | 10/2002 |
| WO | WO-03/061624 | | 7/2003 |
| WO | WO-03/094933 | | 11/2003 |
| WO | WO-2004/016553 A2 | | 2/2004 |
| WO | WO-2004/037274 | | 5/2004 |
| WO | WO-2004/080467 | | 9/2004 |

(Continued)

OTHER PUBLICATIONS

Hutchison AJ Calcitriol, lanthanum carbonate, and other new phosphate binders in the mangement of renal osteodystrophy. Perit Dial Int. 1999, 19 Suppl 2, S408-S412.*

(Continued)

*Primary Examiner*—Johann R Richter
*Assistant Examiner*—Ernst V Arnold
(74) *Attorney, Agent, or Firm*—Darby & Darby P.C.; Shelly M. Fujikawa

(57) ABSTRACT

This invention relates to a chewable lanthanum formulation comprising a pharmaceutically effective amount of a lanthanum compound; and at least one chewable pharmaceutically acceptable excipient. This invention also relates to a pharmaceutical formulation in a tablet or in a powder comprising a pharmaceutically effective amount of a lanthanum compound produced by a process which comprises the steps of: a) powder blending the lanthanum compound and at least one pharmaceutically acceptable excipient in a mixer to form a mixture; or b) powder blending the lanthanum compound and excipients, compressing the resulting combination into a slug material or roller compacting the resulting combination into a strand material, and milling the prepared material into a free flowing mixture; and c) compressing the resulting mixture into a tablet or filing up the resulting mixture in a appropriate container.

12 Claims, 2 Drawing Sheets

FOREIGN PATENT DOCUMENTS

| WO | 2005/018651 | 3/2005 |
|---|---|---|
| WO | WO-2005/041902 | 5/2005 |
| WO | WO-2005/092039 | 10/2005 |
| WO | WO-2005/097072 | 10/2005 |

OTHER PUBLICATIONS

Patent Abstract of Japan abstracting Publication No. 62-145024 Jun. 29, 1987.*

Marketletter Shire's Fosrenol clears bone safety hurdle Jun. 17, 2002, 1 page.*

"Encyclopedia of Pharmaceutical Technology" by Swarbrick et al., vol. 2 (1990); "Biodegradable polyester polymers as drug carriers to clinical pharmacokinetics and pharmacodyanamics"; "Chewable tablets" pp. 397-417.

"Encyclopedia of Pharmaceutical Technology" by Swarbrick et al., vol. 14 (1996); "Self-medication to technology transfer considerations for pharmaceuticals"; "Formulation design", pp. 391-399.

"Calcitriol, lanthanum carbonate, and other new phosphate binders in the management of renal osteodystrophy" by A. J. Hutchison, Perit Dial Int. vol. 12, Suppl. 2, 1999, pp. S408-S412.

International Search Report for PCT/CA2004/001563 mailed Jan. 19, 2005.

Supplementary Partial European Search Report for EP 04 76 1727 completed Sep. 5, 2006.

"Fosrenol"—Retreived from the Internet at URL: http://web.archiveorg/web/20050901114025/www.fosrenol.com/presribingInfo.pdf. Sep. 11, 2005.

Chiang, S-S., et al., "Lanthanum Carbonate (Fosrenolä) Efficacy and Tolerability in the Treatment of Hyperphosphatemic Patients with End Stage Renal Disease," Clinical Nephrology, vol. 63, No. 6, Jun. 2005, p. 461-470.

Cullel-Young, M., et al., "Lanthanum Carbonate—Treatment of Hyperphosphatemia," Drugs of the Future, vol. 28, No. 3, Mar. 1, 2003, p. 224-228.

De Broe, et al., "Lanthanum Carbonate: A new agent in the treatment of hyperphosphataemia in end-stage renal failure", Jun. 2002.

D'Haese et al., "A Multicenter study on the effects of lanthanum carbonate (Fosrenol) and calcium carbonate on renal bone disease in dialysis patients", Kidney International 2003, 63:S73-S78.

Fukagawa, Is Lanthanum carbonate safer and more effective than calcium carbonate for hyperphosphatemia in dialysis patients? Nature Clinical Practice nephrology 2005, 1(1), 20-21.

Korean Office Action dated Oct. 11, 2007 issued for corresponding Korean Patent Application No. 10-2006-7003792. (4 pgs).

Partial Translation and Copy of book titled "the principle and technique of formulations," as cited by Korean Examiner in Oct. 11, 2007 KR Office Action for Korean Patent Application No. 10-2006-7003792, (10 pages).

"III. Dry Granulation" and "V. Direct Compression Tabletting," Pharmacy, Press of People's Health, Oct. 2002, selected extracts (3 pages).

Official Communication dated Apr. 4, 2008, Chinese Patent Application for Invention No. 200480031578.8.

U.S. Appl. No. 11/191,600, Ferdinando et al.

"Pharmaceutical Studies On Drug Delivery Systems For Geriatrics and Cancer Therapies", Yoshuinbobu Fukumori et al., Research and Development of Prophylactic and Therapeutic Agents for Age-Related Diseases in Aging Society. Annual Report 2002-2003, p. 281-285.

*Preparation of Lecithin Microcapsules by a Dilution Method Using the Wurster Process for Intraarterial Administration in Gadolinium Neutron Capture Therapy*, K. Jono et al., Chem Pharm Bull, 1999, vol. 47, No. 1, p. 54-63.

"Design and Preparation of Ethyl Cellulose Microcapsules of Gadopentetate Dimeglumine for Neutron-Capture Therapy Using the Wurster Process", Y. Fukumori et al., Chem Pharm Bull, 1993, vol. 41, No. 6, p. 1144-1148.

"Synthesis and FT-IR study of Ln-glucose-pyridine complexes", L. Zheng et al., AIP Conf. Proc. (1998), vol. 430, Number: Fourier Transform Spectroscopy, pp. 324-326.

"Interaction of metal ions with D-glucose in glassy state-a FT-IR study", Ning Xi et al., Proc. SPIE-Int. Soc. Opt. Eng., 1989, vol. 1145, Number: Int. Conf. Fourier Transform Spectrosc., 7th pp. 405-406.

"*Interaction of Monosaccharides With Metal Ions—NMR Analysis Of Lanthanide Complex*", Kunihiko Izumi, Kagaku Kogyo, 1988, vol. 39, No. 11, pp. 918-924.

"*Fourier transform infrared spectroscopy as a tool for the study of rare earth carbohydrate complexes*", Hong Liang et al. Mikrochim. Acta, 1988, vol. 1, No. 1-6, pp. 215-217.

*NMR Studies of the interaction of metal ions with poly-(1, 4-hexuronates). V. Proton NMR spectra of methyl .alpha.-D-gluo- and methyl .beta.-Dhamamelopyranosides, 1, 6-anhydro- .beta.D-manno, 1,6-anhydro-.beta.-D-talo-and 1, 6-anhydro-.beta.-D-allopyranoses and epi-inositol*, Hans Grasdalen et al., Acta Chem. Scand., Ser. A, 1978, vol. A32, No. 1, pp. 31-39.

"*An analysis of NMR shifts in lanthanide complexes*", H. Bergen et. al. Aust. J Chem., 1977, vol. 30, No. 11, pp. 2361-2369.

Aqueous lanthanide shift reagents. 4. Interaction of praseodymium (3+), neodymium (3+), and europium (3+) ions with xylitol. Origin of induced shifts in polyols, Jacques Reuben, J. Am. Chem. Soc., 1977, vol. 99, No. 6, pp. 1765-1768.

"*Stereospecific contact interactions in the nuclear magnetic resonance spectra of polyol-lanthanide complexes*," Stephen J. Angyal et al., J. Chem. Soc., Chem. Commun., 1974, No. 15, pp. 589-590.

"*NMR spectra of some sugar derivatives in the presence of rare-earth chelates*", P. Girard et al., Tetrahedron, 1971, vol. 27, No. 23, pp. 5911-5920.

"*NMR spectroscopy of (monosaccharides) in the presence of rare earth chelates*", P. Girard et al., Bull. Soc. Chim. Fr., 1970, No. 12, pp. 4515-4516.

"*Chemism of the reaction of neodymium and erbium ions with mono- and disaccharides*" N.S. Poluektov et al., Zh. Neorg. Khim, 1970, vol. 15, No. 5, pp. 1203-1207.

"*Reaction of neodymium and erbium ions with polyhydric alcohols and ascorbic acid*", N.S. Poluektov et al., Ukr. Khim. Zh., 1970, vol. 36, No. 2, pp. 164-169.

"*Nonradiative transfer of excitation energy between rare-earth ions in aqueous solution*", F.S. Quiring, J. Chem. Phys., 1968, vol. 49, No. 5, pp. 2448-2449.

"*Complexes of rare earth elements with disaccharides in solutions*", N.P. Efryushina, et al., Zh. Neorg. Khim, 1967, vol. 12, No. 7, pp. 1855-1861.

"*Complex rare earth compounds with sugars*", N.P. Efryushina et al., Zh. Neorg. Khim, 1967, vol. 12, No. 4, pp. 933-938.

"*Complexes of rare earth elements with some polyhydric alcohols*", N.P. Efryushina, et al., Ukr. Khim. Zh. (Russ. Ed.), 1966, vol. 32, No. 10, pp. 1038-1043.

Limin Yang et al., "*Interactions between metal ions and carbohydrates. Coordination behavior of neutral erythritol to Ca(II) and Lanthanide ions*". Inorganic Chemistry, 42, 19, 5844-5856, Sep. 22, 2003.

"*Lanthanide-saccharide chemistry: synthesis and characterisation of Ce (III)-saccharide complexes*", A. Mukhopadhyay et al., Carbohydrate research (Netherlands) Jan. 29, 2000, 324 (1) p. 30-7.

"*Homogeneous catalyst for DNA hydrolysis (4). Efficient DNA hydrolysis by lanthanide—saccharide complexes*", J. Sumaoka et al., Nucleic acids symposium series (England) 1997, (37) p. 211-2.

"*Calcium and pancreatic beta-cell function. IX. Demonstration of lanthanide-induced inhibition of insulin secretion independent of modifications in transmembrane Ca2+ fluxes.*", P.R. Flatt et al., Endocrinology (United States) Oct. 1980, 107(4) p. 1007-13.

"*Improved cell growth and total flavonoids of Saussurea medusa on solid culture medium supplemented with rare earth elements pharmaceutical production by herb plant callus culture*", XF Yuan et al., Biotechnology Letters (24, 22, 1889-1892) 2002.

"*Promotion of indole alkaloid production in Catharanthus roseus cell cultures by rare earth elements—the effect of cerium, yttrium and neodymium on ajmalicine and catharanthine production by Vinca rosea*", J. Zhao et al., Biotechnol. Lett. (22, 10, 825-28) 2000.

Simultaneous determination of ciprofloxacin and tetracycline in biological fluids based on dual-lanthanide sensitised luminescence using dry reagent chemical technology, R.C. Rodriguez-Diaz et al., Analytica Chimica Acta v 494 n 1-2 Oct. 8, 2003, p. 55-62.

Poluektov et al., Zh. Neorg. Khim, 1970, 15: 1995.

Bhogi B. Sheth et al., "*Chapter :3, Compressed Tablets*", Pharmaceutical Dosage Forms: Tablets, vol. 1, Marcel Dekker, Inc,: New York, 1980, pp. 109-185.

Ralph F. Shangraw, "*Chapter :4, Compressed Tablets by Direct Compression*", Pharmaceutical Dosage Forms: Tablets, vol. 1, Second Edition, Marcel Dekker, Inc.: New York, 1989, pp. 195-246.

Jahan B. Daruwala, "Chapter : 7, Chewable *Tablets*", Pharmaceutical Dosage Forms: Tablets, vol. 1, Marcel Dekker, Inc.: New York, 1980 pp. 289-337.

Properties of CAB-O-SIL® M-5P Fumed Silica, 2004 Cabot Corporation, pp. 1-6.

Influence of CAB-O-SIL® M-5P on the Angle of Repose and Flow Rates of Pharmaceutical Powders, Sep. 2004 Cabot Corporation, pp. 1-10.

Applications of CAB-O-SIL® M-5P Fumed Silica in the Formulation and Design of Solid Dosage Forms, 2004 Cabot Corporation, pp. 1-5.

European Office Action dated Dec. 18, 2006 issued for corresponding European Patent Application No. 04761727.

* cited by examiner

PHARMACEUTICAL FORMULATION COMPRISING LANTHANUM COMPOUNDS

This application claims the benefit of U.S. provisional applications 60/497,560 filed Aug. 26, 2003 and 60/517,078 filed Nov. 5, 2003, which are herein incorporated by reference.

BACKGROUND

Hyperphosphataemia is a particular problem of patients with chronic renal insufficiency using dialysis equipment and with about 70% of patients with end stage renal disease (ESRD). This condition can lead to severe bone problems and metastatic calcification of major organs and is associated with significant morbidity and mortality. Conventional dialysis fails to reduce the levels of phosphate in the blood, so that levels rise in time. Elevated phosphate levels are treated using a combination of dietary restrictions and phosphate-binding agents.

Another problem of patients with chronic renal insufficiency is secondary hyperparathyroidism. It is also important in patients with chronic renal insufficiency to avoid and treat secondary hyperparathyroidism.

Certain forms of lanthanum carbonate have been used to treat hyperphosphataemia in patients with renal failure (see, e.g., JP 1876384). U.S. Pat. No. 5,968,976 describes the preparation and use in a pharmaceutical composition of certain hydrates of lanthanum carbonate for the treatment of hyperphosphataemia.

SUMMARY OF THE INVENTION

Due to their renal problems patients with end stage renal disease or chronic kidney diseases need to limit their liquid intake. There is therefore a need for a formulation of a lanthanum compound that can be taken with no or limited amount of liquid. There is also a need for a chewable formulation. There is also a need for a formulation that is palatable to the patient especially under conditions as dry as possible. There is also a need for a formulation that is compressible into a tablet.

This invention relates to a chewable lanthanum formulation comprising:
  a) a pharmaceutically effective amount of a lanthanum compound; and
  b) at least one chewable pharmaceutically acceptable excipient.

This invention relates to a palatable lanthanum formulation comprising:
  a) a pharmaceutically effective amount of a lanthanum compound; and
  b) at least one pharmaceutically acceptable excipient, the formulation being palatable to a mammal, e.g., humans, cats, dogs, etc.

This invention relates to a sprinklable lanthanum formulation comprising;
  a) a pharmaceutically effective amount of a lanthanum compound; and
  b) at least one pharmaceutically acceptable excipient.

This invention relates to a method for controlling hyperphosphataemia in a patient comprising administering a therapeutically effective amount of a lanthanum compound in a palatable formulation.

This invention relates to a method for controlling hyperphosphataemia in a patient comprising administering a therapeutically effective amount of a lanthanum compound in a chewable formulation.

This invention relates to a method for controlling hyperphosphataemia in a patient comprising administering a therapeutically effective amount of a lanthanum compound in a sprinklable formulation.

This invention relates to a pharmaceutical formulation in a tablet or in a powder comprising a pharmaceutically effective amount of a lanthanum compound produced by a process which comprises the steps of:
  a) powder blending the lanthanum compound and at least one pharmaceutically acceptable excipient in a mixer to form a mixture and;
  b) compressing the mixture into a tablet or filing up the resulting mixture in an appropriate container.

This invention relates to a pharmaceutical formulation in a tablet or in a powder comprising a pharmaceutically effective amount of a lanthanum compound produced by a process which comprises the steps of:
  a) powder blending the lanthanum compound and at least one pharmaceutically acceptable excipient in a mixer to form a mixture; or
  b) powder blending the lanthanum compound and excipients, compressing the resulting combination into a slug material or roller compacting the resulting combination into a strand material, and milling the prepared material into a free flowing mixture; and
  c) compressing the mixture into a tablet or filing up the resulting mixture in a appropriate container.

This invention relates to a pharmaceutical formulation in a tablet or in a powder comprising a pharmaceutically effective amount of a lanthanum compound produced by a process which comprises the steps of compressing the lanthanum compound into a slug material or roller compacting into a strand material, and milling the prepared material into a free flowing material, then blending with excipients, the resulting combination is compressed into a tablet or filing up the resulting mixture in a appropriate container.

In a preferred aspect, such formulation is also chewable and/or sprinklable and/or palatable and the lanthanum carbonate is in a desired hydration state.

This invention relates to a pharmaceutical formulation in a chewable tablet comprising a pharmaceutically effective amount of a lanthanum compound produced by a process which comprises the steps of:
  a) powder blending the lanthanum compound and at least one pharmaceutically acceptable excipient in a mixer to form a mixture; and
  b) compressing the mixture into a tablet.

This invention relates to a process for preparing a formulation of a lanthanum compound which comprises the steps of:
  a) powder blending the lanthanum compound and at least one pharmaceutically acceptable excipient in a mixer to form a mixture.

This invention relates to a process for preparing a tablet formulation of a lanthanum compound which comprises the steps of:
  a) powder blending the lanthanum compound and at least one pharmaceutically acceptable excipient in a mixer to form a mixture; and
  b) compressing the mixture into a tablet.

In one aspect, the present invention is directed to a process for obtaining the formulation of the present invention. It should be noted that the hydration state of the lanthanum compound present in the formulation of the present invention is relevant to the biological properties of the product. It is therefore desirable to maintain a stable hydration status of the lanthanum compound. For example, when the starting lanthanum compound is lanthanum carbonate as defined herein, it is desired to maintain hydration levels constant throughout the formulation process. This represents an additional challenge to obtaining a tablet or powder that is acceptable to the patient. It is important to mention that certain lanthanum compounds, such as lanthanum carbonate have poor flow characteristics. These poor flow characteristics also represent a further challenge when preparing formulations that have high drug load, as is the case for lanthanum carbonate while maintaining a dose size that is acceptable and palatable to the patient. With drugs which have a specific hydration status, granulating with water or solvents and drying is not always advisable as this can affect the hydration status of the drug. In some cases other techniques such as roller compaction/slugging/milling/compression may be used to improve the flow. If roller compaction/slugging/milling/compression is not suitable, direct compression can be used to make tablets. Again, if the drug has poor flow characteristics and is in a high dose, then direct compression can be difficult due to poor flow. If drug is in low dose (for example 100 mg/tablet or less), then a higher proportion of excipients can be used to ameliorate the flow problems but for lanthanum carbonate hydrate, where the drug is present in higher yield, the amount of excipients added must be limited to ensure the tablet is a suitable size. Therefore, there is a need for a formulation process in which allows maintaining the hydration status of the lanthanum compound within desired ranges. In a further embodiment, the process does not require the use of a wet granulation step. In a further embodiment, the formulation process of the present invention does not involve a drying step.

In one embodiment, the invention relates to such a method for treating hyperphosphataemia in a renal failure patient, including but not limited to a patient receiving dialysis and a patient with end-stage renal disease (ESRD), comprising administering a therapeutically effective amount of a lanthanum compound.

In one embodiment, the invention relates to such a method for treating a chronic kidney disease patient comprising administering a therapeutically effective amount of a lanthanum compound.

In another embodiment, the invention relates to a method for controlling hyperparathyroidism in a patient with chronic renal insufficiency comprising administering a therapeutically effective amount of a lanthanum compound, preferably lanthanum carbonate.

In yet another embodiment, the invention relates to a method for treating hyperparathyroidism in a patient with chronic renal insufficiency comprising administering a therapeutically effective amount of a lanthanum compound, preferably lanthanum carbonate.

In another embodiment, the lanthanum compound is administered in such a formulation such that plasma levels of lanthanum are low, e.g., at least as good as those provided by a mean concentration curve where $C_{max}$, $T_{max}$ and AUC are preferably less than 1.5 ng/ml, about 12 hours, and less than 50 ng·hr/ml, respectively, for a dose of 3 g per day (e.g., 1 g three times a day), such as is achieved in the prior art. In a more preferred embodiment, $C_{max}$ and AUC are less than 1.1 ng/ml and less than 32 ng·hr/ml, and in a most preferred embodiment, $C_{max}$ and AUC are less than 0.5 ng/ml and less than 20 ng·hr/ml, of such dosage. $T_{max}$ values are essentially unaffected by dose and $C_{max}$ and AUC values vary linearly with dosage. All of these parameters have their highly conventional meanings.

In another embodiment, the invention relates to a method of treating hyperphosphataemia comprising administering to a patient in need thereof such a lanthanum carbonate formulation.

Preferred lanthanum compounds include lanthanum carbonate compounds. Lanthanum carbonate compounds refer to all forms of lanthanum carbonate.

In a preferred embodiment, the invention relates to lanthanum carbonate of the general formula:

$$La_2(CO_3)_3 \cdot xH_2O$$

where x has a value from 3 to 8, from 3 to 7, from 3 to 6, preferably from 3 to 5, more preferably from 3 to 4, more preferably from 3 to 4.5, preferably from 4 to 5, most preferably 3.4, most preferably x has an average value of 4; for the preparation of a medicament for the treatment of hyperphosphataemia by administration into the gastrointestinal tract; see e.g., U.S. Pat. No. 5,968,976 which is incorporated herein by reference. The hydration level of the lanthanum compound can be measured by methods well known in the art, such as thermal analysis (TGA).

In one aspect, the excipients used in the formulation of the present invention are suitable for administration to renally impaired patients. In a further aspect, the excipients include diluents, binders, and lubricants/glidants. It is understood that other agents such as disintegrant, colors, flavors/sweeteners can be added to the formulation.

The diluents can be chosen from dextrates, corn syrup, oligosaccharide, isomaltooligosaccharide, glucose, lycasin, xylitol, lactitol, erythritol, mannitol, isomaltose, polydextrose, dextrin, starch, fructose, xylitol, maltodextrin, maltitol, isomalt, lactose, sorbitol, microcrystalline cellulose (such as avicel), sucrose based diluent-binders (such as Nutab, Di-Pac or Sugartab), confectioner's sugar, calcium sulfate dihydrate, calcium lactate trihydrate, hydrolysed starches (such as Emdex or Celutab), dextrose (such as Cerelose), inositol, hydrolyzed cereal solids (such as Maltrons or Mor-Rex), amylose or glycine.

The diluents can be chosen from dextrates, starch, lactose, mannitol, sorbitol, microcrystalline cellulose (such as avicel), sucrose based diluent-binders (such as Nutab, Di-Pac or Sugartab), confectioner's sugar, calcium sulfate dihydrate, calcium lactate trihydrate, hydrolysed starches (such as Emdex or Celutab), dextrose (such as Cerelose), inositol, hydrolyzed cereal solids (such as Maltrons or Mor-Rex), amylose or glycine.

In a further embodiment, the diluents can be chosen from dextrates, starch, lactose, mannitol, sorbitol, microcrystalline cellulose (such as avicel), sucrose based diluent-binders (such as Nutab, Di-Pac or Sugartab), calcium sulfate dihydrate, calcium lactate trihydrate, hydrolysed starches (such as Emdex or Celutab), dextrose (such as Cerelose), inositol, or amylose.

In a further embodiment, the diluent is chosen from dextrates, fructose, xylitol, erythritol, maltodextrin, dextrose, maltitol, isomalt or glucose.

In a further embodiment, the diluent is dextrates.

In a further embodiment, lubricant/glidants and blending/flow agents can be chosen from for example magnesium stearate, talc, polyethylene glycol, silica, colloidal anhydrous silica, hydrogenated vegetable oils, glyceryl behenate or glyceryl monostearate.

In a further embodiment, lubricant/glidants and blending/flow agents can be chosen from for example magnesium stearate, talc, polyethylene glycol, silica or colloidal anhydrous silica In one aspect the invention is directed to a chewable formulation comprising:

| Formulation | wt % range from about to about |
|---|---|
| Lanthanum (elemental) | 5-50 |
| Diluent(s) (e.g., dextrates (hydrated)) | 10-90 |
| Blending/flow agent(s)-Lubricant(s) (e.g., colloidal anhydrous silica and/or magnesium stearate) | 0.1-6.0 |

In a further aspect, the invention is directed to a formulation comprising:

| Formulation | wt % range from about to about |
|---|---|
| Lanthanum (elemental) | 10-40 |
| Diluent(s) (e.g., dextrates (hydrated)) | 40-80 |
| Blending/flow agent(s)-Lubricant(s) (e.g., colloidal anhydrous silica and/or., magnesium stearate) | 0.1-5.0 |

In a further aspect, the invention is directed to a chewable formulation comprising:

| Formulation | wt % range from about to about |
|---|---|
| Lanthanum (elemental) | 20-30 |
| Diluent(s) (e.g., dextrates (hydrated)) | 30-60 |
| Blending/flow agent(s)-Lubricant(s) (e.g., colloidal anhydrous silica and/or., magnesium stearate) | 0.1-5.0 |

In a further aspect, the invention is directed to a formulation comprising:

| Formulation | wt % range from about to about |
|---|---|
| Lanthanum (elemental) | 20-30 |
| Diluent(s) (e.g., dextrates (hydrated)) | 30-50 |
| Blending/flow agent(s)-Lubricant(s) (e.g., colloidal anhydrous silica and/or., magnesium stearate) | 0.1-5.0 |

In a further aspect, the invention is directed to a formulation comprising:

| Formulation | wt % range from about to about |
|---|---|
| Lanthanum (elemental) | 10-30 |
| Diluent(s) (e.g., dextrates (hydrated)) | 24-60 |
| Blending/flow agent(s)-Lubricant(s) (e.g., colloidal anhydrous silica and/or magnesium stearate) | 0.1-5.0 |

In a further aspect, the invention is directed to a formulation comprising:

| Formulation | wt % range from about to about |
|---|---|
| Lanthanum (elemental) | 20-30 |
| Diluent(s) (e.g., dextrates (hydrated)) | 40-60 |
| Blending/flow agent(s)-Lubricant(s) (e.g., colloidal anhydrous silica and/or., magnesium stearate) | 0.1-5.0 |

In a further aspect, the invention is directed to a chewable formulation comprising:

| Formulation | wt % range from about to about |
|---|---|
| Lanthanum (elemental) | 20-27 |
| Diluent(s) (e.g., dextrates (hydrated)) | 42-58 |
| Blending/flow agent(s)-Lubricant(s) (e.g., colloidal anhydrous silica and/or., magnesium stearate) | 0.1-4.0 |

These formulations are also sprinklable when manufactured in a conventional, applicable dosage form, e.g. beads, crushed tablets, powder, sieved granules, all are palatable. For patient s that have a hard time chewing tablets, the formulation can either sprinkled onto a spoon or onto food if needed.

Tablets may be coated according to methods well known in the art.

It may be advantageous to incorporate an antioxidant, for example ascorbic acid, butylated hydroxyanisole or hydroquinone in the formulations of the invention to enhance their storage life.

Alternatively, administration may be conducted in an uninterrupted regimen; such a regimen may be a long term regimen, e.g. a permanent regimen.

In one aspect the invention is directed to a pharmaceutical formulation in a tablet containing an amount of elemental lanthanum selected from 250 mg, 500 mg, 750 mg and 1000 mg, produced by a process which comprises the steps of:

a) dry admixing a lanthanum compound and excipient in a mixer to form a mixture; and b) compressing the mixture into tablets using a single punch or rotary tablet machine.

A typical dosage for an adult may be, e.g., 750 mg-3000 mg daily. The dose can be divided and taken with each meal, for example 250-1000 mg, e.g., three times per day. Serum plasma levels can be monitored weekly until an optimal serum phosphate level is reached conventionally.

Lanthanum is a rare earth element with an atomic number of 57. The properties of lanthanum make this agent a good candidate as a useful phosphate binder. It has a high affinity for binding phosphorous and in the form of its carbonate salt, has a low solubility that limits gastrointestinal absorption. In addition, the phosphate binding is independent of pH, it possesses a low toxic potential based on the $LD_{50}$, it is palatable, abundant, and has limited effects on serum electrolyte concentrations (Hutchison, A J et al. (1998) Perit. Dial. Int. 18(Suppl 2): S38.

It will be understood that the dosages of formulations and the duration of administration according to the invention will vary depending on the requirements of the particular subject. The precise dosage regime will be determined by the attending physician or veterinary surgeon who will, inter alia, consider factors such as body weight, age and symptoms (if any). The formulations may if desired incorporate one or more further active ingredients.

In a further embodiment, the present invention relates to a veterinary use of a lanthanum compound for the treatment of a non-human animal, e.g. a companion animal suffering from hyperphosphaetemia comprising the step of administering a pharmaceutically acceptable amount of a lanthanum compound to such an animal, e.g. a companion animal in need of such treatment.

Oral use of medicaments by animals has been commonly quite difficult, due to reluctance of the animals to ingest tablets, pills or medicated food, especially if the drug has an unpleasant taste or odour. Medicament when administered orally, for example, as tablets, even when mixed with habitual food, is frequently rejected by the animal, and the treatment either cannot be effected or must be applied by force, but only to a restricted and thus usually insufficient and inconsistent extent.

There has been limited success in orally administering medicaments to companion animals. For example, U.S. Pat. No. 5,824,336 describes the need for a palatable anti-helminthic composition for companion animals and is specifically directed to a chewable tablet composition of flubendazole that is palatable to dogs.

More particularly, veterinary handbooks for cat owners typically caution against breaking up pills into powders. For example, in the Cat Owner's Home Veterinary Handbook by Carlson D. G. et al. (1983, First Edition, Howell Book House Inc.) this point is emphasized on the basis that powders make an unpleasant taste which is poorly tolerated. Furthermore, it advises that medications specifically intended to be added to a cat's ration can be disguised by adding brewer's yeast, cheese or strong fish oil. This reference work also describes more elaborate ways in which tablet and liquid formulations can be directly administered to a cat and particularly, how the cat is held, the mouth opened and the dosage form placed into the cat's mouth, to ensure consumption.

It is also recognized that controlling the diet in companion animals is more difficult and therefore that controlling the intake of phosphates is comparatively difficult relative to human subjects.

It is also notorious that the sense of smell (strongly correlated with taste) of companion animals is especially acute as compared with human subjects. Accordingly, there exists a need for a palatable agent which can be readily used to treat hyperphosphataemia and control associated hypercalcemia especially in companion animals, including, for example dogs and cats. As renal disease is frequently diagnosed in older cats, improved medications for this disease condition are urgently required for this species.

It has now been discovered that lanthanum compounds can be administered to animals, including companion animals in a palatable amount effective to mitigate hyperphosphataemia. Further, it has been discovered that the degree to which a lanthanum compound is palatable in such animals permits such compounds to be administered in a dosage form in which special coatings, masking components and administration procedures are not required to encourage consumption, especially when put into the animal's food ration. In particular, it has been discovered that lanthanum compounds can be administered to cats in an amount effective to mitigate hyperphosphataemia when in a particulate form for admixture with food.

Accordingly, in one aspect the invention is directed to a method for treating hyperphosphaetemia in a companion animal comprising the step of administering a pharmaceutically acceptable amount of a lanthanum compound to a companion animal in need of such treatment.

During the dosing regimen, administration may be effected once or more times per day, for example once, twice, three or four times per day.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. In case of conflict, the present specification, including definitions, will control. In addition, the materials, methods, and examples are illustrative only and not intended to be limiting.

Without further elaboration, it is believed that one skilled in the art can, using the preceding description, utilized the present invention to its fullest extent. The following preferred embodiments are, therefore, to be construed as merely illustrative, and not limitative of the remainder of the disclosure in any way whatsoever.

EXAMPLES

Example 1

Figure 1:
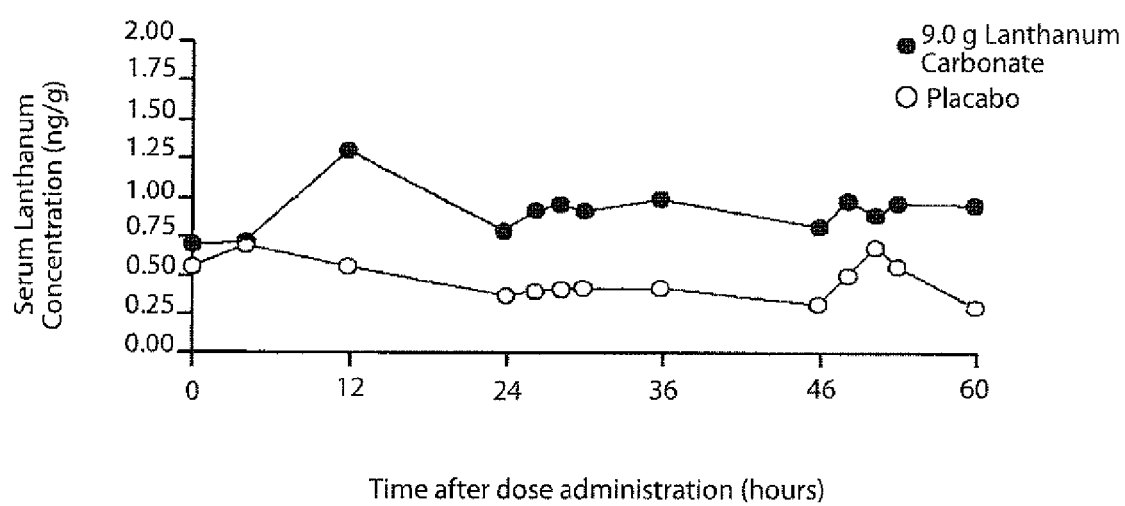
FIG. 1 shows the mean concentration of lanthanum in serum (lanthanum given at maximally tolerated dose for 72 hours).
Figure 2:
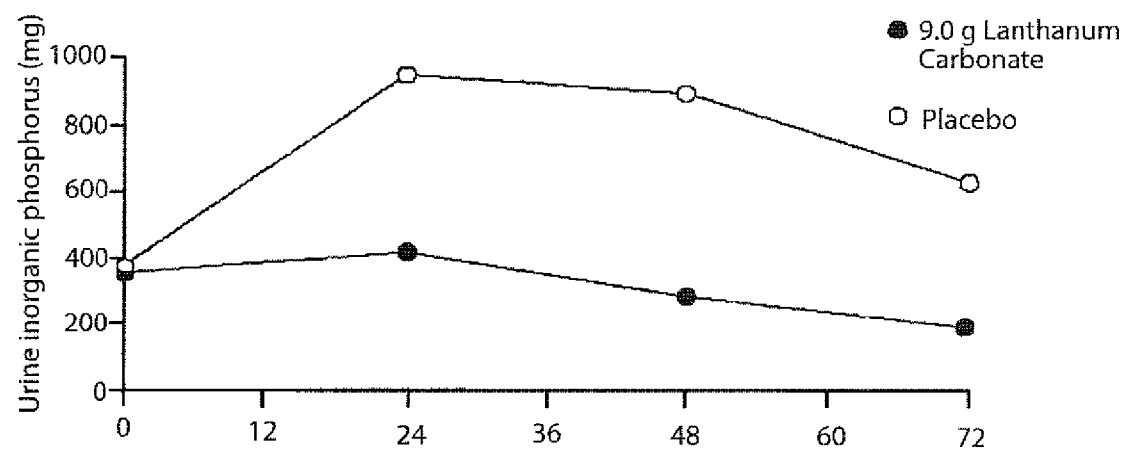
FIG. 2 shows the mean concentration of inorganic phosphorus in urine.

Preparation of Lanthanum Carbonate Hydrate Chewable Tablets (250 mg, 500 mg, 750 mg and 1000 mg).

The manufacturing process involves sieving and blending the active ingredient with the excipients followed by direct compression. More specifically the steps are as follows for the 250 mg and 500 mg Formulation A tablets:
 a) Pass the lanthanum carbonate, dextrates and colloidal silicon dioxide through a screen of at least 16-mesh into a suitable blender and blend for about 20 minutes.
 b) Pass the talc (optional) and magnesium stearate through a 30-mesh screen and add to the blender and blend for about 5 minutes.
 c) Compress the blend using standard tooling to the target compression weight.

The following tablets were prepared as generally described in the example:

TABLE 1A

Formulation A

| Ingredient | 250 mg tablet | 500 mg tablet | Function |
|---|---|---|---|
| Active Ingredient | | | |
| Lanthanum (III) carbonate hydrate | 477.0 mg | 954.0 mg | Active |
| Other Ingredients | | | |
| Dextrates (hydrated) | 1247.0 mg | 2494.0 mg | Diluent |
| Colloidal anhydrous silica | 36.0 mg | 72.0 mg | Improve blend/flow |
| Purified talc | 30.0 mg | 60.0 mg | Lubricant/Glidant |
| Magnesium stearate | 10.0 mg | 20.0 mg | Lubricant |
| TOTAL | 1800 mg | 3600 mg | |

TABLE 1B

Formulation B

| | 250 mg Tablet | 500 mg Tablet | 750 mg Tablet | 1000 mg Tablet |
|---|---|---|---|---|
| Dosage form | Chewable Tablet | Chewable Tablet | Chewable Tablet | Chewable Tablet |
| Tablet Diameter Formulation | 13 mm | 18 mm | 20 mm | 22 mm |
| Lanthanum (elemental) | 250 mg | 500 mg | 750 mg | 1000 mg |
| Lanthanum carbonate hydrate[1] | 477 mg | 954 mg | 1431 mg | 1908 mg |
| Dextrates (hydrated) | 533.2 mg | 1066.4 mg | 1599.6 mg | 2132.8 mg |
| Colloidal silicon dioxide | 21.2 mg | 42.4 mg | 63.6 mg | 84.4 mg |
| Magnesium stearate | 10.6 mg | 21.2 mg | 31.8 mg | 42.4 mg |
| Total Weight | 1042 mg | 2084 mg | 3126 mg | 4168 mg |

Example 2

Summary of Studies Conducted with Formulation A

1. Several Studies Summary

The ranges of mean concentrations of lanthanum in plasma obtained at designated time points within several studies in randomized patients among five PhaseII/III studies are summarized in Table 2.

TABLE 2

| Study Number | Dose Range of Lanthanum (mg/day) | Duration of Treatment (Weeks) | Range of Mean Plasma Lanthanum Levels (SD), ng/ml |
|---|---|---|---|
| 1 | 375-2250 Dose Titration (Part 1) | 4 | 0.16 (0.31)-0.69 (0.55)[a] |
| | 375-2250 Maintenance Fixed Dose (Part 2) | 4 | 0.39 (0.37)-0.67 (0.98)[a] |
| 2 | 225-2250 Fixed Dose Levels | 6 | 0.21 (0.22)-0.86 (0.91) |
| 3 | 750-3000 Adjustable Dose Levels | 49 | 0.38 (0.25)-0.67 (0.65) |
| 4 | 375-3000 Dose Titration to Fixed Dose Levels | 10 | 0.35 (0.44)-0.78 (1.05) |
| 5 | 750-3000 Dose Titration to Fixed Dose Levels | 52 | 0.4 (0.76)-0.6 (1.15) |

[a]Units are ng/gm. Conversion to ng/ml, multiply plasma concentrations by 1.054, density of plasma.

The ranges and the upper range values of the mean plasma lanthanum levels are similar across the PhaseII/III studies with the highest mean level at <1 ng/ml. The range values were similarly low as the values of $C_{max}$ that were determined in earlier studies.

2. This study evaluates the primary and safety pharmacology of a conventional non-calcium anti-hyperphosphataemia treatment, lanthanum carbonate (LC).

Methods

The in vitro phosphate binding efficacy of LC is assessed at the relevant gastrointestinal pHs of 3, 5 and 7 using aluminum hydroxide (AH) and calcium-salts as comparators. In vivo dietary phosphate binding is compared with AH, calcium carbonate (CC) and sevelamer hydrochloride (SH) (1000 mg binder/kg/day) in $5/6^{th}$ nephrectomized rats are dosed daily for 6 weeks and using urine phosphate excretion as the primary end-point. The potential for unwanted pharmacological effects of LC on CNS, cardiovascular, respiratory and GI systems is evaluated in mice, rats and dogs at doses up to 2000 mg/kg/day.

Results

In vitro, LC is equipotent with AH and significantly more potent than CC or calcium acetate. LC is most effective (97.5% phosphate bound) at pH 3, but also has good efficacy at pH 5 and 7. In $5/6^{th}$ nephrectomized rats, LC is equipotent with AH and significantly more potent than CC or SH at reducing urinary phosphate excretion, a sensitive marker of dietary phosphate binding in this model. At doses up to 2000 mg/kg, LC has no direct effects on serum calcium, vitamin D or PTH levels and no adverse pharmacological actions on cardiovascular, respiratory or GI systems in mice, rats or dogs. No acute or long-term effects on CNS function occur in mice or dogs in Irwin and neurotoxicity screens. LC has no pro- or anti-convulsive activity and no effects on locomotor activity in mice.

This study indicates that LC is a selective and potent phosphate binder with similar efficacy to aluminum hydroxide and a low potential for adverse safety pharmacology.

3. This preclinical study is conducted to investigate the long-term toxicity of conventional lanthanum carbonate (LC).

Methods

Single- and multiple-dose oral and iv toxicity studies with LC in mice, rats and dogs use doses up to 2000 mg/kg/day (po) (×17 a human dose of 1000 mg t.i.d.) and 1 mg/kg/day (iv). Plasma LC levels are up to 20,000 times those in dialysis patients. The studies range in duration up to 1 year in dogs and 2 years (life-time exposure) in rodents. Studies in $5/6^{th}$ nephrectomized rats evaluated any influence of renal impairment on the toxicity profile. The studies include clinical assessments, ECG, ophthalmoscopy, haematology, urinanalysis, serum chemistry, plasma and tissue LC exposure, and histopathological examination of over 40 tissues. Full programs to assess genetic toxicity, reproduction toxicity and carcinogenicity are also conducted.

Results

LC is very well tolerated, with no effects on appearance, growth or survival in the life-time studies. Adaptive changes in the rodent stomach (not observed in dogs) are the only findings at high oral doses. Rats with impaired renal function have comparable tissue exposure to normal rats, and also tolerate LC very well. Histomorphometry reveals no potential for direct bone toxicity. Some indirect effects on mineralization are due to phosphate depletion caused by excessive dietary binding at high doses. Lanthanum is not genotoxic or carcinogenic, and does not adversely affect any stage of reproduction.

4. This study is conducted to compare conventional lanthanum carbonate (LC) with other therapies (calcium or aluminum salts, or sevelamer hydrochloride).

Methods

This 2-year multicenter, randomized, open-label, parallel-group trial consists of a 1- to 3-week washout period, a 6-week titration phase and a long-term maintenance phase. Hemodialysis patients with serum phosphorus >5.9 mg/dL (>1.9 mmol/L) receive either LC (375-3000 mg/day elemental lanthanum) or their pre-study phosphate binder. The primary aim of the study is to evaluate safety and tolerability over 2 years. The main efficacy endpoint is control of serum phosphorus $\leq 5.9$ mg/dL.

Results

In total, 647 patients receive LC and 642 receive standard therapy (calcium agents: 78%; sevelamer: 16%). Average total treatment exposure is higher with standard therapy than with LC (422.2±258.5 vs. 304.1±253.8 days). Treatment-emergent adverse events occur with greater frequency in the standard therapy group than the LC group included hypercalcemia (10.4 vs. 3.4%), diarrhea (27.4 vs. 19.8%), abdominal pain (20.9 vs. 14.1%) and dyspepsia (14.8 vs. 8.2%). Serious adverse events are also more frequent in the standard-treatment group (65.4 vs. 51.0%). However, this is likely to be complicated by the difference in treatment exposure between groups. Plasma lanthanum remains very low throughout treatment (mean level: 0.5-0.6 ng/mL). Similar proportions of patients in both groups have effective phosphorus control during maintenance therapy (46.3% vs. 41.3%; standard therapy vs. LC at 2 years).

LC is at least as well tolerated as other current phosphate binders over the long term, and exhibits similar efficacy in maintaining serum phosphate control over a 2-year period.

5. This study compares the efficacy, safety and tolerability of conventional lanthanum carbonate (LC) with those of calcium carbonate (CC) in a randomized, open-label, multicenter trial.

Methods After a 1- to 3-week washout period, haemodialysis patients with hyperphosphataemia (serum phosphorus >1.80 mmol/L [5.6 mg/dL]) are randomized to receive LC (375-3000 mg/day lanthanum; n=533) or CC (1500-9000 mg/day calcium; n=267). Patients are then titrated to a maintenance dose of either drug that provides optimal phosphate control (serum phosphorus <1.80 mmol/L) within 5 weeks. Both LC- and CC-treated patients who have controlled serum phosphorus levels after titration receive maintenance treatment for 20 weeks more.

Results

Control of serum phosphorus levels is achieved in similar proportions of patients treated with LC and CC (Week 9: 67.9% vs. 65.8%; Week 25: 65.8% vs. 63.9%). LC is associated with a significantly greater decrease in calcium x phosphorus product than CC at Week 9 (−1.80 vs. −1.35 mmol 2/L2; P=0.009) and a numerically greater decrease at Week 25 (−1.59 vs. −1.26 mmol 2/L2). Plasma levels of lanthanum are very low throughout treatment with LC: 0.49 ng/mL at the highest lanthanum dose administered at Week 25. Adverse events are generally mild or moderate in severity, occurring in 77.7% of patients receiving LC and 79.8% of patients receiving CC. Hypercalcaemia occurs substantially more frequently in patients receiving CC (20.2%) compared with those receiving LC (0.4%).

LC shows equivalent efficacy to CC in controlling serum phosphorus in patients with end-stage renal disease. LC is well tolerated, with a lower risk of hypercalcaemia than CC.

6. This study reports the results from a 6-month, open-label extension of a previous 6-month, randomized clinical trial comparing conventional LC with calcium carbonate (CC).

Methods

Following 6 months of randomized treatment in the initial trial, patients who receive CC for 6 months are switched to a 5-week titration with LC (CC/LC group) to control serum phosphorus at $\leq 1.8$ mmol/L (5.6 mg/dL). Those who initially receive LC in the randomized trial continue to receive LC at their established maintenance dose (LC/LC group; total treatment duration, 49 weeks).

Results

In total, 518 patients entered the extension study: 185 in the CC/LC group and 333 in the LC/LC group. Overall, 375 patients (72.4%) completed the study: 113 (61.1%) in the CC/LC group and 262 (78.7%) in the LC/LC group. Serum phosphorus levels are maintained at around 1.8 mmol/L (5.6 mg/dL) in both groups over 24 weeks: mean endpoint values were 1.76 mmol/L in the LC/LC group and 1.83 mmol/L in the CC/LC group. At the end of the extension period, serum phosphorus is controlled in 63.3% of the LC/LC group, compared with 58.3% of the CC/LC group. The most common treatment-emergent adverse events are gastrointestinal, while those considered to be related to study treatment are reported by 17% of LC/LC patients and 31% of CC/LC patients. Hypercalcemic episodes are reported by 0.3% of patients in the LC/LC group and 2.7% of patients in the CC/LC group.

LC is well tolerated and effective for a period of at least 1 year. The reduced incidence of hypercalcemia observed with LC in short-term trials is maintained for 1 year.

7. Safety and efficacy are assessed in a large-scale, randomized, 1-year trial of the effects of prolonged treatment with conventional lanthanum carbonate (LC) or calcium carbonate (CC) on bone parameters.

Methods

Chronic renal failure patients undergoing haemodialysis or continuous ambulatory peritoneal dialysis are randomized (1:1) to receive either LC (up to 3750 mg/day lanthanum; n=49) or CC (up to 9000 mg/day calcium; n=49) for 50 weeks. Safety analyses include adverse events, vital signs and plasma lanthanum. Efficacy assessments include serum phosphorus and parathyroid hormone (PTH).

Results

All 98 patients were included in the intent-to-treat efficacy and safety population. Adverse-event profiles were similar with LC and CC, but hypercalcemic events (serum calcium >2.65 mmol/L) were much less frequent with LC (6%) than with CC (35%). There were no clinically relevant changes in vital signs during LC or CC therapy. Plasma lanthanum levels were similar in the LC- and CC-treated patients (range, 0.31-0.11 ng/mL) at baseline, and were higher in LC-treated patients (<0.03-1.95 ng/mL) than in CC-treated patients (all <0.03 ng/mL) at endpoint. Plasma lanthanum reached steady state early in the study in LC-treated patients, and was similar between Weeks 8 and 52. LC and CC provided similar control of serum phosphorus. Baseline mean (± SD) values were 1.72±0.39 and 1.87±0.52 mmol/L, and endpoint values were 1.79±0.47 and 1.65±0.54 mmol/L with LC and CC, respectively. Serum PTH remained stable with LC over 1 year, but decreased with CC.

LC appeared to be equally well tolerated and showed equivalent efficacy to CC, but with a greatly reduced risk of hypercalcemia over 1 year of treatment. As in other long-term studies, prolonged LC therapy did not result in plasma lanthanum accumulation.

8. This study evaluated the efficacy and safety of conventional lanthanum carbonate (LC) in an ethnic Chinese population. LC tablets providing 500 mg lanthanum were evaluated. These higher-strength tablets could reduce overall pill burden—an important issue affecting patient compliance.

Methods

The study comprised 3 parts: a 1- to 3-week screening and washout phase, a 4-week, open-label, dose-titration phase with LC, and a 4-week, double-blind, maintenance phase in which patients were randomized (1:1) to receive LC or placebo. LC was administered as chewable tablets providing 250 or 500 mg lanthanum. Male and female haemodialysis patients were included who had serum phosphorus levels >5.6 mg/dL (1.8 mmol/L) following washout of their previous phosphate binder. The study enrolled 103 patients. The primary efficacy endpoint was the serum phosphorus level obtained at the last week of double-blind treatment. The control of serum phosphorus to ≦5.6 mg/dL (1.8 mmol/L) was the main secondary efficacy endpoint. Other secondary efficacy measures included the profile of serum phosphorus during titration, and serum parathyroid hormone, calcium and calcium x phosphorus product levels. The safety and tolerability profile of LC was assessed by monitoring of adverse events and vital signs at each study visit. Full biochemical and haematological screens were also undertaken, and plasma levels of lanthanum were measured throughout the study.

9. Renal osteodystrophy (ROD) is an important complication of hyperphosphataemia, associated with significant patient morbidity. Aluminum-based phosphate binders have been associated with bone toxicity and have thus added to the existing difficulties of ROD. This study was designed to demonstrate the lack of similar toxicity for conventional lanthanum carbonate (LC) and to compare its long-term effects on bone with those of calcium carbonate (CC).

Methods

In total, 98 patients were randomized to treatment with either LC (n=49) or CC (n=49) for 1 year. Tetracycline-labeled bone biopsies were taken at baseline and after 1 year of open-label treatment, and full histomorphometry analyses performed. Bone alkaline phosphatase activity and serum parathyroid hormone (PTH) and calcitriol levels were also measured.

Results

Bone biopsies from baseline and following 1 year of treatment were available from 33 LC- and 30 CC-treated patients. Neither group demonstrated aluminum-like bone toxicity. After 1 year, 5/7 LC- and 3/7 CC-treated patients with osteomalacia or adynamic bone at baseline, and 4/5 LC- and 3/6 CC-treated patients with high-turnover ROD at baseline had evolved away from these severe types of ROD. Only one patient in the LC group evolved towards adynamic bone vs. six in the CC group. There were no significant differences in bone alkaline phosphatase activities or serum calcitriol levels between the treatment groups or at the end of the study (vs. baseline). Serum PTH levels remained stable in the LC group, whereas reductions were seen in the CC group, with a greater variation in data range.

Over 1 year, dialysis patients treated with LC showed a greater evolution away from the more severe types of ROD compared with CC-treated patients. Other parameters of bone status showed no significant change in LC-treated patients. LC may therefore have an advantage over conventional phosphate binders when treating ROD.

The preceding examples can be repeated with similar success by substituting the generically or specifically described reactants and/or operating conditions of the invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A lanthanum carbonate pharmaceutical formulation in a chewable tablet, comprising lanthanum carbonate in an amount of from about 200 mg to about 1000 mg elemental lanthanum in the proportion of about 10 to about 40 wt % of the formulation as elemental lanthanum and pharmaceutically acceptable excipients comprising a diluent in an amount from about 40 to about 80 wt % of the formulation and a flow agent in an amount from about 0.1 to about 5.0 wt % of the formulation, produced by a process which comprises the steps of:
   a. blending the lanthanum carbonate and the pharmaceutically acceptable excipients to form a mixture; or
   b. blending the lanthanum carbonate and the pharmaceutically acceptable excipients, compressing the resulting combination into a slug material or roller compacting the resulting combination into a strand material, and milling the prepared material into a free flowing mixture; and
   c. compressing the mixture formed in steps a or b into a tablet,
   wherein the process is performed without wet granulation or drying, the diluent is dextrates, corn syrup, oligosaccharide, isomaltooligosaccharide, glucose, lycasin, xylitol, lactitol, erythritol, mannitol, isomaltose, polydextrose, dextrin, starch, fructose, xylitol, maltodextrin, maltitol, isomalt, lactose, sorbitol, microcrystalline cellulose, sucrose based diluent-binders, confectioner's sugar, calcium sulfate dihydrate, calcium lactate trihydrate, hydrolysed starches, dextrose, inositol, hydrolyzed cereal solids, amylase, or glycine, and the flow agent is magnesium stearate, talc, polyethylene glycol, silica, colloidal anhydrous silica, hydrogenated vegetable oils, glyceryl behenate, or glyceryl monostearate.

2. A lanthanum carbonate pharmaceutical formulation in a chewable tablet, comprising lanthanum carbonate in an amount of from about 200 mg to about 1000 mg elemental lanthanum in the proportion of about 10 to about 40 wt % of the formulation as elemental lanthanum and pharmaceutically acceptable excipients comprising a diluent in an amount from about 40 to about 80 wt % of the formulation and a flow agent in an amount from about 0.1 to about 5.0 wt % of the formulation, produced by a process which comprises the steps of:

a. compressing the lanthanum carbonate into a slug material or roller compacting the lanthanum carbonate into a strand material,
b. milling the slug or strand material into a free flowing material,
c. blending the free flowing material with the pharmaceutically acceptable excipients to form a mixture, and
d. compressing the mixture into a tablet,
wherein the process is performed without wet granulation or drying, the diluent is dextrates, corn syrup, oligosaccharide, isomaltooligosaccharide, glucose, lycasin, xylitol, lactitol, erythritol, mannitol, isomaltose, polydextrose, dextrin, starch, fructose, xylitol, maltodextrin, maltitol, isomalt, lactose, sorbitol, microcrystalline cellulose, sucrose based diluent-binders, confectioner's sugar, calcium sulfate dihydrate, calcium lactate trihydrate, hydrolysed starches, dextrose, inositol, hydrolyzed cereal solids, amylase, or glycine, and the flow agent is magnesium stearate, talc, polyethylene glycol, silica, colloidal anhydrous silica, hydrogenated vegetable oils, glyceryl behenate, or glyceryl monostearate.

3. The formulation of claim 1, wherein the lanthanum carbonate has the formula:

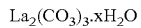

where x has a value from 3 to 8.

4. The formulation of claim 3, wherein x has a value from about 4 to about 5.

5. The formulation of claim 1, wherein the diluent is dextrates or sorbitol.

6. The formulation of claim 1, wherein the flow agent is colloidal anhydrous silica in an amount of about 2 wt % of the formulation.

7. The chewable lanthanum carbonate pharmaceutical tablet of claim 1 for the treatment of chronic renal insufficiency, comprising the following ingredients:

| Ingredient | % by weight |
| --- | --- |
| lanthanum carbonate | 26.5 |
| dextrates | 69.3 |
| colloidal anhydrous silica | 2.0 |
| talc | 1.7 |
| magnesium stearate | 0.5 | wherein the lanthanum carbonate is hydrated having a water content of about 4 moles of water.

8. The chewable lanthanum carbonate pharmaceutical tablet of claim 1 for the treatment of chronic renal insufficiency comprising the following ingredients:

| Ingredient | % by weight |
| --- | --- |
| lanthanum carbonate | 45.8 |
| dextrates | 51.2 |
| colloidal anhydrous silica | 2.0 |
| magnesium stearate | 1.0 | wherein the lanthanum carbonate is hydrated having a water content of about 4 moles of water.

9. A lanthanum carbonate pharmaceutical formulation in a powder, comprising lanthanum carbonate in an amount of from about 200 mg to about 1000 mg elemental lanthanum in the proportion of about 10 to about 40 wt % of the formulation as elemental lanthanum and pharmaceutically acceptable excipients comprising a diluent in an amount from about 40 to about 80 wt % of the formulation and a flow agent in an amount from about 0.1 to about 5.0 wt % of the formulation, produced by a process which comprises the steps of:

a. blending the lanthanum carbonate and the pharmaceutically acceptable excipients,
b. compressing the resulting combination into a slug material or roller compacting the resulting combination into a strand material, and
c. milling the prepared material into a free flowing powder mixture,
wherein the process is performed without wet granulation or drying, the diluent is dextrates, corn syrup, oligosaccharide, isomaltooligosaccharide, glucose, lycasin, xylitol, lactitol, erythritol, mannitol, isomaltose, polydextrose, dextrin, starch, fructose, xylitol, maltodextrin, maltitol, isomalt, lactose, sorbitol, microcrystalline cellulose, sucrose based diluent-binders, confectioner's sugar, calcium sulfate dihydrate, calcium lactate trihydrate, hydrolysed starches, dextrose, inositol, hydrolyzed cereal solids, amylase, or glycine, and the flow agent is magnesium stearate, talc, polyethylene glycol, silica, colloidal anhydrous silica, hydrogenated vegetable oils, glyceryl behenate, or glyceryl monostearate.

10. A lanthanum carbonate pharmaceutical formulation in a powder comprising, lanthanum carbonate in an amount of from about 200 mg to about 1000 mg elemental lanthanum in the proportion of about 10 to about 40 wt % of the formulation as elemental lanthanum and pharmaceutically acceptable excipients comprising a diluent in an amount from about 40 to about 80 wt % of the formulation and a flow agent in an amount from about 0.1 to about 5.0 wt % of the formulation, produced by a process which comprises the steps of:

a. compressing the lanthanum carbonate into a slug material or roller compacting the lanthanum carbonate into a strand material,
b. milling the slug or strand material into a free flowing material, and
c. blending the free flowing powder material with the pharmaceutically acceptable excipients to form a mixture,
wherein the process is performed without wet granulation or drying, the diluent is dextrates, corn syrup, oligosaccharide, isomaltooligosaccharide, glucose, lycasin, xylitol, lactitol, erythritol, mannitol, isomaltose, polydextrose, dextrin, starch, fructose, xylitol, maltodextrin, maltitol, isomalt, lactose, sorbitol, microcrystalline cellulose, sucrose based diluent-binders, confectioner's sugar, calcium sulfate dihydrate, calcium lactate trihydrate, hydrolysed starches, dextrose, inositol, hydrolyzed cereal solids, amylase, or glycine, and the flow agent is magnesium stearate, talc, polyethylene glycol, silica, colloidal anhydrous silica, hydrogenated vegetable oils, glyceryl behenate, or glyceryl monostearate.

11. The formulation of claim 1, produced by the process which comprises the steps of:

a. blending the lanthanum carbonate and the pharmaceutically acceptable excipients to form a mixture; and
b. compressing the mixture into a tablet.

12. The lanthanum carbonate pharmaceutical formulation of claim 1, wherein the lanthanum carbonate is in an amount from about 20 to about 30 wt % lanthanum, as the element.

* * * * *

UNITED STATES PATENT AND TRADEMARK OFFICE
CERTIFICATE OF CORRECTION

| | | |
|---|---|---|
| PATENT NO. | : 7,465,465 B2 | Page 1 of 1 |
| APPLICATION NO. | : 10/926330 | |
| DATED | : December 16, 2008 | |
| INVENTOR(S) | : Haslam et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 44 days.

Signed and Sealed this
Eleventh Day of January, 2011

David J. Kappos
*Director of the United States Patent and Trademark Office*